United States Patent
Butters et al.

(10) Patent No.: US 7,193,083 B2
(45) Date of Patent: Mar. 20, 2007

(54) PREPARATION OF TRIAZOLES BY ORGANOMETALLIC ADDITION TO KETONES AND INTERMEDIATES THEREFOR

(75) Inventors: Michael Butters, Sandwich (GB); Alan John Pettman, Sandwich (GB)

(73) Assignee: Pfizer, Inc., San Diego, CA (US)

( * ) Notice: Subject to any disclaimer, the term of this patent is extended or adjusted under 35 U.S.C. 154(b) by 0 days.

(21) Appl. No.: 11/120,739

(22) Filed: May 2, 2005

(65) Prior Publication Data

US 2005/0272747 A1    Dec. 8, 2005

Related U.S. Application Data

(62) Division of application No. 10/368,928, filed on Feb. 19, 2003, now Pat. No. 6,946,555, which is a division of application No. 09/011,346, filed as application No. PCT/EP96/03376 on Jul. 26, 1996, now Pat. No. 6,586,594.

(51) Int. Cl.
    *C07D 403/10*    (2006.01)
(52) U.S. Cl. ..................................... 544/333
(58) Field of Classification Search ................. 544/333
    See application file for complete search history.

(56) References Cited

U.S. PATENT DOCUMENTS

| 5,364,938 | A | * | 11/1994 | Dickinson et al. | .......... | 544/333 |
| 5,567,817 | A | * | 10/1996 | Ray et al. | ..................... | 544/333 |
| 6,586,594 | B1 | * | 7/2003 | Butters et al. | ............... | 544/333 |

* cited by examiner

Primary Examiner—Patricia L. Morris
(74) Attorney, Agent, or Firm—Elsa Djuardi; Bryan C. Zielinski

(57) ABSTRACT

The invention provides a process for the preparation of a compound of the formula:

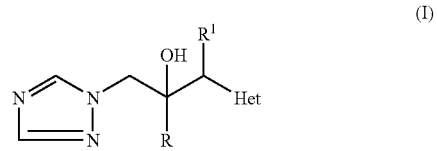

(I)

or an acid addition or base salt thereof,
wherein
R is phenyl optionally substituted by 1 to 3 substituents each independently selected from halo and trifluoromethyl;
$R^1$ is $C_1$–$C_6$ alkyl; and
"Het" is pyrimidinyl optionally substituted by 1 to 3 substituents each independently selected from $C_1$–$C_4$ alkyl, $C_1$–$C_4$ alkoxy, halo, oxo, benzyl and benzyloxy,
comprising reaction of a compound of the formula:

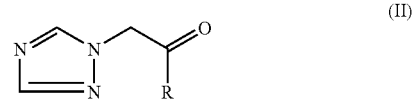

(II)

wherein R is as previously defined for a compound of the formula (I), with a compound of the formula:

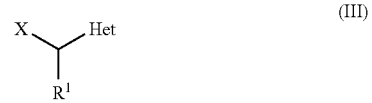

(III)

wherein $R^1$ and "Het" are as previously defined for a compound of the formula (I) and X is chloro, bromo or iodo, in the presence of zinc, iodine and/or a Lewis acid and an aprotic organic solvent: said process being optionally followed by conversion of the compound of the formula (I) to an acid addition or base salt thereof.

17 Claims, No Drawings

PREPARATION OF TRIAZOLES BY ORGANOMETALLIC ADDITION TO KETONES AND INTERMEDIATES THEREFOR

This application is a divisional application of a non-provisional application Ser. No. 10/368,928, filed Feb. 19, 2003, now U.S. Pat. No. 6,946,555, which is a divisional application of a non-provisional application Ser. No. 09/011,346, filed 4 Feb. 1998, now U.S. Pat. No. 6,586,594, which is the national stage of international application No. PCT/EP96/03376, filed 26 Jul. 1996, which is published in English under International Publication No. 97/06160.

BACKGROUND OF THE INVENTION

This invention relates to a process for the preparation of alcohols by the addition of organometallic reagents to ketones. More particularly, this invention relates to the reaction of 1-phenyl-2-(1H-1,2,4-triazol-1-yl)ethanone derivatives with organometallic compounds derived from alpha-haloalkylpyrimidines to form tertiary alcohols.

The reaction of organometallic compounds derived from alkyl halides with aldehydes and ketones to form secondary and tertiary alcohols, respectively, is well established in the field of organic chemistry. Many different metals and metal derivatives have been reported as being useful in this type of reaction, including lithium, magnesium, aluminium, tin and zinc, together with salts thereof. For example, A. R. Gangloff et al, J. Org. Chem., 57, 4797–4799 (1992) discloses that 2-(bromomethyl)-4-carbethoxy-1,3-oxazole reacts with zinc dust to form an organozinc derivative which undergoes nucleophilic addition to aldehydes and ketones. Also, Chollet et al, Synth. Comm., 19 (11 and 12), 2167–2173 (1989) reports the reaction of organozinc derivatives of bromoesters with aldehydes and ketones.

Certain compounds prepared according to the present process are disclosed in European Patent Application Publication numbers 0357241 and 0440372.

It has now been surprisingly found that certain 1-phenyl-2-(1H-1,2,4-triazol-1-yl)ethanone derivatives may be reacted with organometallic compounds derived from certain alpha-haloalkylpyrimidine derivatives to form tertiary alcohols in good to excellent yields and with high stereoselectivity using reaction conditions that are particularly suitable for the bulk synthesis of the product.

This finding has been found to be particularly useful for the synthesis of (2R,3S/2S,3R)-3-(4-chloro-5-fluoropyrimidin-6-yl)-2-(2,4-difluorophenyl)-1-(1H-1,2,4-triazol-1-yl)butan-2-ol, a key intermediate for the preparation of (2R,3S)-2-(2,4-difluorophenyl)-3-(5-fluoropyrimidin-4-yl)-1-(1H-1,2,4-triazol-1-yl)butan-2-ol, a compound having antifungal activity. The syntheses of both of these compounds have been described in European Patent Application Publication number 0440372. In this Application, (2R,3S/2S,3R)-3-(4-chloro-5-fluoropyrimidin-6-yl)-2-(2,4-difluorophenyl)-1-(1H-1,2,4-triazol-1-yl)butan-2-ol is prepared by the chromatographic separation of the two pairs of enantiomers obtained from the addition of an organolithium derivative of 4-chloro-6-ethyl-5-fluoropyrimidine to 1-(2,4-difluorophenyl)-2-(1H-1,2,4-triazol-1-yl)ethanone at from −70 to −50° C. The best stereoselectivity that has been obtained in this addition is a 1.1:1 molar ratio in favour of the 2R,3S/2S,3R enantiomeric pair with the total isolated yield of all four stereoisomers being only about 50%, the low yield being thought to be due to a competing enolisation reaction. These factors, coupled with the need to operate the addition reaction at very low temperatures and under very dilute conditions, together with the difficulty in separating approximately equimolar amounts of the two pairs of enantiomers at the end of the reaction with the 2R,3R/2S,3S enantiomeric pair being unwanted, mean that the process is extremely unsuitable for the economic preparation of the required 2R,3S/2S,3R intermediate on a large scale.

In contrast, for example, it has now been found that a 9:1 molar ratio of the 2R,3S/2S,3R to the 2R,3R/2S,3S enantiomeric pair of 3-(4-chloro-5-fluoropyrimidin-6-yl)-2-(2,4-difluorophenyl)-1-(1H-1,2,4-triazol-1-yl)butan-2-ol and a 65% isolated total yield of all the enantiomers (as the hydrochloride salts) can be obtained under the reaction conditions according to the present invention that are highly suitable for large scale synthesis of the product.

However, higher isolated yields have been obtained and higher molar ratios (both in situ and in respect of isolated product) have been determined by varying the reaction conditions in accordance with the present invention.

Similar results have been obtained with a range of alpha-haloalkyl-pyrimidine substrates.

Considerable economic advantages result from the yields and stereospecificity achieved.

The present invention provides a process for the preparation of a compound of the formula:

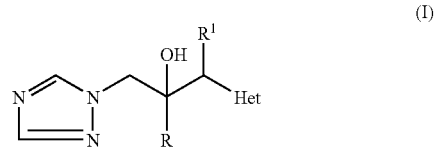

or an acid addition or base salt thereof, wherein

R is phenyl optionally substituted by 1 to 3 substituents each independently selected from halo and trifluoromethyl;

$R^1$ is $C_1$–$C_6$ alkyl; and

"Het" is pyrimidinyl optionally substituted by 1 to 3 substituents each independently selected from $C_1$–$C_4$ alkyl, $C_1$–$C_4$ alkoxy, halo, oxo, benzyl and benzyloxy, comprising reaction of a compound of the formula:

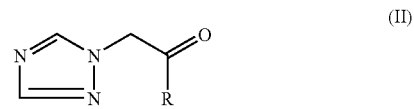

wherein R is as previously defined for a compound of the formula (I), with a compound of the formula:

wherein $R^1$ and "Het" are as previously defined for a compound of the formula (I) and X is chloro, bromo or iodo, in the presence of zinc, iodine and/or a Lewis acid and an aprotic organic solvent: said process being optionally followed by formation of an acid addition or base salt of the product.

Optionally, lead can also be present in the reaction, either as the metal per se or in the form of a suitable salt, e.g. a lead (II) halide. It can be added separately or be inherently present in the zinc used.

In the above definitions, alkyl and alkoxy groups containing three or more carbon atoms may be straight- or branched-chain and "halo" means fluoro, chloro, bromo or iodo.

Preferably, R is phenyl optionally substituted by 1 to 3 halo substituents.

More preferably, R is phenyl substituted by 1 or 2 substituents each independently selected from fluoro and chloro.

Yet more preferably, R is phenyl substituted by 1 or 2 fluoro substituents.

Most preferably, R is 2,4-difluorophenyl.

Preferably, $R^1$ is $C_1$–$C_4$ alkyl.

More preferably, $R^1$ is methyl or ethyl.

Most preferably, $R^1$ is methyl.

Preferably, "Het" is pyrimidinyl optionally substituted by 1 to 3 substituents each independently selected from halo, oxo and benzyl.

More preferably, "Het" is pyrimidinyl optionally substituted by 1 to 3 substituents each independently selected from fluoro, chloro, oxo and benzyl.

Yet more preferably, "Het" is pyrimidinyl substituted by 1 to 3 substituents each independently selected from fluoro and chloro.

Preferred examples of "Het" include pyrimidin-4-yl, 4-chloro-5-fluoropyrimidin-6-yl, 5-fluoropyrimidin-4-yl, 2-chloro-5-fluoropyrimidin-6-yl, 2,4-dichloro-5-fluoropyrimidin-6-yl, 4-chloropyrimidin-6-yl and 1-benzyl-5-fluoropyrimidin-6-on-4-yl.

Most preferably, "Het" is 4-chloro-5-fluoropyrimidin-6-yl.

Preferably, X is bromo or iodo.

Most preferably, X is bromo.

The compound of the formula (II) may be an enolisable ketone. Most preferably, the compound of formula (II) is 1-(2,4-difluorophenyl)-2-(1H-1,2,4-triazol-1-yl)ethanone.

Preferably the compound of the formula (III) is selected from 6-(1-bromoethyl)-2,4-dichloro-5-fluoropyrimidine, 6-(1-bromoethyl)-4-chloro-5-fluoropyrimidine, 6-(1-bromoethyl)-2-chloro-5-fluoropyrimidine, 4-(1-bromoethyl)pyrimidine, 4-(1-bromoethyl)-6-chloropyrimidine, 4-(1-bromoethyl)-5-fluoropyrimidine and 1-benzyl-4-(1-bromoethyl)-5-fluoropyrimidin-6-one.

Most preferably, the compound of the formula (III) is 6-(1-bromoethyl)-4-chloro-5-fluoropyrimidine.

The reaction is carried out in the presence of a suitable aprotic organic solvent such as tetrahydrofuran, toluene, 1,2-dimethoxyethane or methylene chloride, or a mixture of two or more thereof. It is highly desirable to dry the solvent before use to remove substantially all traces of water. Drying can be achieved using a desiccant such as magnesium sulphate, sodium sulphate or molecular sieves, by distillation from a metal such as lithium, sodium or potassium or by azeotropic distillation.

The preferred solvent for the reaction is tetrahydrofuran.

It is also preferable to carry out the reaction under a dry, inert atmosphere such as by using dry nitrogen or argon gas.

The zinc used in the reaction may be zinc powder derived from a commercial source or it may be freshly generated in situ by the reduction of a zinc halide (e.g. zinc chloride) using lithium, sodium or potassium (see, e.g., R. D. Rieke, Acc. Chem. Res., 10, 301 (1977)). The zinc powder may be activated prior to use by stirring a slurry of the powder for several hours in a suitable solvent, e.g. tetrahydrofuran.

Optionally, the reaction is carried out in the additional presence of lead.

The zinc powder obtained commercially may contain small amounts of lead as an impurity and the lead content can be up to about 2000 parts per million (0.20 weight %) depending on the source. However, it is generally preferred to increase the lead content by adding lead in the form of lead powder to the reaction mixture. Lead powder is commercially available.

Preferably, when used, the amount of lead present in the reaction is 2000 ppm (0.2 wt %) or more relative to the amount of zinc present. More preferably, the amount of lead present is from 2000 to 100,000 ppm (0.2 to 10 weight %). Most preferably, the amount of lead present is about 50,000 ppm (5 wt %).

Iodine is generally used in its commercially available crystalline form. It is suspected that its role in the reaction is in the in situ generation of zinc iodide, possibly, when lead is also present, in conjunction with lead (II) iodide as well, both of which may function as catalysts.

Iodine, when used, may be introduced into the reaction vessel before, during or after the compounds of the formulae (II) and (III) have been added. Alternatively, it can be added in at least two stages, for example, one portion can be added to the reaction vessel before, and the second portion can be added when, the compounds of the formulae (II) and (III) are added.

Suitable Lewis acids for use in the reaction include zinc chloride, zinc bromide, zinc iodide, titanium (IV) isopropoxide, chlorotitanium triisopropoxide, titanium tetrachloride, trimethyl borate, boron trifluoride (etherate), iron (III) chloride and diethylaluminium chloride.

Preferred Lewis acids are zinc bromide, zinc iodide and, particularly, zinc chloride.

Iodine is preferably used rather than separately adding a Lewis acid.

Optionally, both iodine and a Lewis acid may be used in the above process.

The reaction may be carried out at from −15° C. to the reflux temperature of the mixture. Preferably, it is carried out at from −10 to +30° C. and most preferably from −10° C. to +15° C.

The reaction almost certainly proceeds via formation of an organozinc species derived from the in situ reaction of zinc with a compound of the formula (III) that is used as a starting material.

The reaction may be carried out by the following general procedure.

Iodine and/or a suitable Lewis acid are/is added to a stirred mixture of zinc, optionally lead, and a suitable aprotic organic solvent. The mixture is cooled and a solution of a compound of the formula (II), a compound of the formula (III) and, optionally, further iodine in a suitable aprotic organic solvent is added, cooling the mixture during the addition. The mixture is stirred for a further short period before being warmed to room temperature. The reaction is quenched by adding glacial acetic acid followed by water and conventional work-up techniques can then be used in order to isolate the required product.

The process is optionally followed by formation of an acid addition or a base salt of the product. Formation of an acid addition salt is preferred and suitable salts include the hydrochloride, hydrobromide, hydroiodide, sulphate, nitrate, methanesulphonate, camphorsulphonate, R-(−)-10-camphorsulphonate, (+)-3-bromo-10-camphorsulphonate, (−)-3-bromo-8-camphorsulphonate, phosphate, para-toluenesulphonate and benzenesulphonate salts. The hydrochloride salt is particularly preferred.

A compound of the formula (I) produced by the process of the invention contains two or more asymmetric carbon atoms and therefore exists in four or more stereoisomeric forms.

The reaction generally proceeds with high stereoselectivity in favour of the (2R,3S/2S,3R) enantiomeric pair of a compound of the formula (I), i.e.

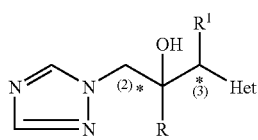

(I)

where the asterixes (★) indicate the subject asymmetric carbon atoms.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. Resolution of enantiomers of a compound of the formula (I) may be achieved by H.P.L.C. of the corresponding racemate using a suitable chiral support or by fractional crystallisation of the diastereoisomeric salts formed by reaction of the corresponding racemate with a suitable optically active acid, e.g. R-(−)-10-camphorsulphonic acid.

The process is preferably used to prepare 3-(4-chloro-5-fluoropyrimidin-6-yl)-2-(2,4-difluorophenyl)-1-(1H-1,2,4-triazol-1-yl)butan-2-ol from the starting materials 1-(2,4-difluorophenyl)-2-(1H-1,2,4-triazol-1-yl)ethanone and 6-(1-bromoethyl)-4-chloro-5-fluoropyrimidine. High stereoselectivity can be achieved in the reaction with, for example, a 9:1 molar ratio of the 2R,3S/2S,3R to the 2R,3R/2S,3S enantiomeric pair being obtained if the reaction conditions are carefully controlled. In addition, for example, a 65% isolated total yield (as the hydrochloride salts) of all the enantiomers has been obtained.

The reaction product, which contains a far higher proportion of (2R,3S/2S,3R)-3-(4-chloro-5-fluoropyrimidin-6-yl)-2-(2,4-difluorophenyl)-1-(1H-1,2,4-triazol-1-yl)butan-2-ol hydrochloride, can be reduced to provide (2R,3S/2S,3R)-2-(2,4-difluorophenyl)-3-(5-fluoropyrimidin-4-yl)-1-(1H-1,2,3,4-triazol-1-yl)butan-2-ol which can be resolved to provide (2R,3S)-2-(2,4-difluorophenyl)-3-(5-fluoropyrimidin-4-yl)-1-(1H-1,2,4-triazol-1-yl)butan-2-ol by the method described in European Patent Application Publication number 0440372.

In a further aspect, the present invention provides a process for the preparation of a compound of the formula:

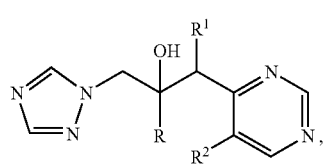

(IV)

or an acid addition salt thereof, wherein R and $R^1$ are as previously defined for a compound of the formula (I) and $R^2$ is H or fluoro, which comprises the steps of:
(a) reaction of a compound of the formula:

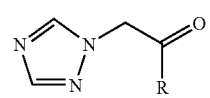

(II)

wherein R is as defined for a compound of the formula (IV), with a compound of the formula:

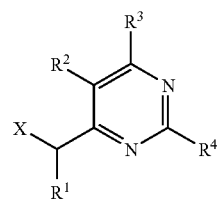

(IIIA)

wherein X is chloro, bromo or iodo, $R^1$ and $R^2$ are as previously defined for a compound of the formula (IV) and either $R^3$ and $R^4$ are each independently selected from chloro and bromo or one of $R^3$ and $R^4$ is chloro or bromo and the other is H, in the presence of zinc, iodine and/or a Lewis acid and an aprotic organic solvent, to provide a compound of the formula:

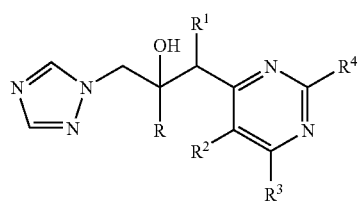

(IA)

wherein R, $R^1$, $R^2$, $R^3$ and $R^4$ are as previously defined for this step (a);
(b) optionally converting the compound of the formula (IA) to an acid addition salt thereof;
(c) reduction of the compound of the formula (IA) or an acid addition salt thereof to provide the compound of the formula (IV); and
(d) optionally converting the compound of the formula (IV) to an acid addition salt thereof.

The reactions conditions, including the preferred conditions, used for step (a) are as previously described for the preparation of a compound of the formula (I). Again, optionally, lead can also be present in step (a).

The reduction in step (c) can be carried out under any conditions suitable for the replacement of one or more of the $R^3/R^4$ groups where $R^3/R^4$ is chloro or bromo by hydrogen.

The reduction may be carried out under conventional hydrogenation conditions using a suitable catalyst, e.g. palladium-on-charcoal, optionally in the presence of a suitable base, e.g. sodium acetate, and in a suitable solvent, e.g. ethanol, under a hydrogen atmosphere.

Preferably, the reduction is carried out under transfer hydrogenation conditions using a suitable catalyst, e.g. palladium or rhodium, a suitable hydrogen donor, e.g. ammonium or potassium formate, and in a suitable solvent, e.g. methanol. The reaction is preferably carried out at the reflux temperature of the solvent and under a nitrogen atmosphere.

Examples of acid additions salts in step (b) include the hydrochloride, nitrate, methanesulphonate, p-toluenesulphonate, camphorsulphonate, R-(−)-10-camphorsulphonate, (+)-3-bromo-10-camphorsulphonate and (−)-3-bromo-8-camphorsulphonate salts. Preferred acid addition salts in step (b) are the hydrochloride, methanesulphonate and p-toluenesulphonate salts.

A preferred acid addition salt in step (d) is the R-(−)-10-camphorsulphonate which may be used to resolve enantiomers of the compound of the formula (IV). A S-(+)-10-camphorsulphonate salt may also be generated and used for this purpose.

In this process for the preparation of a compound of the formula (IV):
(i) Preferably, R is phenyl optionally substituted by 1 to 3 halo substituents.
  More preferably, R is phenyl substituted by 1 or 2 substituents each independently selected from fluoro and chloro.
  Yet more preferably, R is phenyl substituted by 1 or 2 fluoro substituents. Most preferably, R is 2,4-difluorophenyl.
(ii) Preferably, $R^1$ is $C_1$–$C_4$ alkyl.
  More preferably, $R^1$ is methyl or ethyl.
  Most preferably, $R^1$ is methyl.
(iii) Preferably, X is bromo or iodo.
  Most preferably, X is bromo.
(iv) Preferably, $R^2$ is fluoro.
(v) Preferably, $R^3$ is chloro and $R^4$ is H, $R^3$ is H and $R^4$ is chloro or $R^3$ and $R^4$ are both chloro.
(vi) Preferred compounds of the formula (IIIA) include:
  6-(1-bromoethyl)-2,4-dichloro-5-fluoropyrimidine,
  6-(1-bromoethyl)-4-chloro-5-fluoropyrimidine,
  6-(1-bromoethyl)-2-chloro-5-fluoropyrimidine and
  4-(1-bromoethyl)-6-chloropyrimidine.
(vii) Preferred compounds of the formula (IA) include:
  3-(4-chloro-5-fluoropyrimidin-6-yl)-2-(2,4-difluorophenyl)-1-(1H-1,2,4-triazol-1-yl)butan-2-ol,
  3-(2-chloro-5-fluoropyrimidin-6-yl)-2-(2,4-difluorophenyl)-1-(1H-1,2,4-triazol-1-yl)butan-2-ol,
  3-(2,4-dichloro-5-fluoropyrimidin-6-yl)-2-(2,4-difluorophenyl)-1-(1H-1,2,4-triazol-1-yl)butan-2-ol and
  3-(4-chloropyrimidin-6-yl)-2-(2,4-difluorophenyl)-1-(1H-1,2,4-triazol-1-yl)butan-2-ol,
  and the acid addition salts thereof, particularly the hydrochloride, methanesulphonate and p-toluenesulphonate salts.
(viii) Preferred compounds of the formula (IV) include:
  2-(2,4-difluorophenyl)-3-(5-fluoropyrimidin-4-yl)-1-(1H-1,2,4-triazol-1-yl)butan-2-ol and
  2-(2,4-difluorophenyl)-3-(pyrimidin-4-yl)-1-(1H-1,2,4-triazol-1-yl)butan-2-ol,
  and the acid addition salts thereof, particularly the S-(+)- or R-(−)-10-camphorsulphonate salts.

The preparations of the starting materials used in the process of the present invention are conventional and appropriate reagents and reaction conditions for their preparation as well as procedures for isolating the desired products will be well known to those skilled in the art with reference to literature precedents and the Preparations hereto.

The present invention also provides the following novel compounds:

(i) (2R,3S)-3-(4-chloro-5-fluoropyrimidin-6-yl)-2-(2,4-difluorophenyl)-1-(1H-1,2,4-triazol-1-yl)butan-2-ol;
(ii) an acid addition salt of (2R,3S/2S,3R)- or (2R,3S)-3-(4-chloro-5-fluoropyrimidin-6-yl)-2-(2,4-difluorophenyl)-1-(1H-1,2,4-triazol-1-yl)butan-2-ol and preferably a hydrochloride, nitrate, methanesulphonate, p-toluenesulphonate, camphorsulphonate, R-(−)-10-camphorsulphonate, (+)-3-bromo-10-camphorsulphonate or (−)-3-bromo-8-camphorsulphonate salt;
(iii) 3-(2,4-dichloro-5-fluoropyrimidin-6-yl)-2-(2,4-difluorophenyl)-1-(1H-1,2,4-triazol-1-yl)butan-2-ol, or the (2R,3S/2S,3R)- or (2R,3S)- form thereof, or an acid addition salt of any thereof;
(iv) 3-(2-chloro-5-fluoropyrimidin-6-yl)-2-(2,4-difluorophenyl)-1-(1H-1,2,4-triazol-1-yl)butan-2-ol, or the (2R,3S/2S,3R)- or (2R,3S)- form thereof, or an acid addition salt of any thereof;
(v) 3-(1-benzyl-5-fluoropyrimidin-6-on-4-yl)-2-(2,4-difluorophenyl)-1-(1H-1,2,4-triazol-1-yl)butan-2-ol, or the (2R,3S/2S,3R)- or (2R,3S)- form thereof, or an acid addition salt of any thereof;
(vi) 3-(4-chloropyrimidin-6-yl)-2-(2,4-difluorophenyl)-1-(1H-1,2,4-triazol-1-yl)butan-2-ol, or the (2R,3S/2S,3R)- or (2R,3S)- form thereof, or an acid addition salt of any thereof;
(vii) 6-(1-bromoethyl)-2,4-dichloro-5-fluoropyrimidine;
(viii) 4-(1-bromoethyl)-6-chloropyrimidine;
(ix) 6-(1-bromoethyl)-4-chloro-5-fluoropyrimidine;
(x) 1-benzyl-4-(1-bromoethyl)-5-fluoropyrimidin-6-one;
(xi) 6-(1-bromoethyl)-2-chloro-5-fluoropyrimidine;
(xii) 4-(1-bromoethyl)-5-fluoropyrimidine;
(xiii) 2-chloro-6-ethyl-5-fluoro-4-hydroxypyrimidine, ammonium salt.

The following Examples illustrate the process of the present invention:—

EXAMPLE 1

9:1★(2R,3S/2S,3R)-:(2R,3R/2S,3S)-3-(4-Chloro-5-fluoropyrimidin-6-yl)-2-(2,4-difluorophenyl)-1-(1H-1,2,4-triazol-1-yl)butan-2-ol hydrochloride

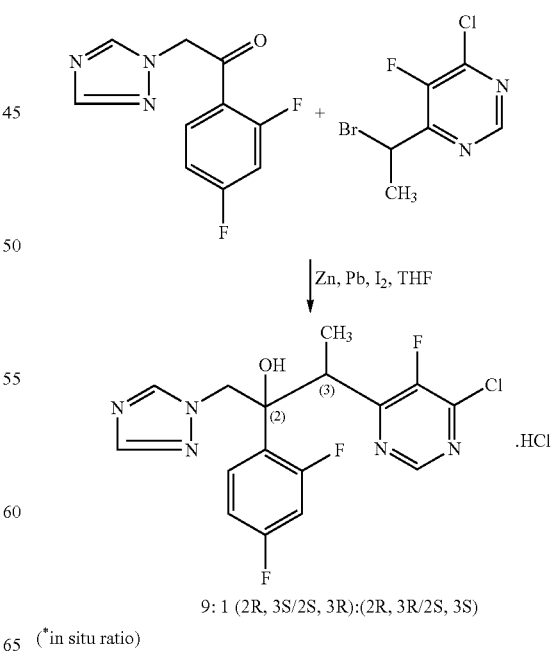

9:1 (2R, 3S/2S, 3R):(2R, 3R/2S, 3S)

(★in situ ratio)

A stirred mixture of zinc powder (Britannia Alloys) (9.35 kg), lead (325 mesh, Aldrich) (0.47 kg) and tetrahydrofuran (53 L) was heated under reflux under a nitrogen atmosphere for 3 hours. The mixture was then cooled to 25° C. and stirring continued for 16 hours. A solution of iodine (7.42 kg) in tetrahydrofuran (21 L) was added over 80 minutes and the reaction temperature was allowed to rise to 45° C. during the addition. The mixture was then cooled to from 0 to −5° C. A solution of 1-(2,4-difluorophenyl)-2-(1H-1,2,4-triazol-1-yl)ethanone (6.53 kg) and 6-(1-bromoethyl)-4-chloro-5-fluoropyrimidine (see Preparation 1) (7.01 kg) in tetrahydrofuran (53 L) was then added maintaining the reaction temperature below +5° C. during the addition. The mixture was warmed to 25° C. and glacial acetic acid (8.84 kg) and water (84 L) added. The solid metal residues were separated by decantation and 60 liters of tetrahydrofuran removed by distillation under reduced pressure. Ethyl acetate (76 kg) was added and the distillation continued to remove 165 liters of solvent. The mixture was cooled and extracted with ethyl acetate (2×84 L), the combined extracts washed with a solution of disodium ethylenediaminetetraacetate dihydrate (3.22 kg) in water (161 L), followed by saturated brine (30 L).

The ratio of the enantiomeric pairs contained in the organic layer was determined by HPLC analysis using a 25 cm C18 Dynamax 60 angstrom reverse phase column, a mobile phase consisting of 65:35, by volume, acetonitrile: water and a flow rate of 1 ml/min. The detector was set at 254 nm. This analysis showed a 9:1 molar ratio of the 2R,3S/2S,3R (RT=5.53 min.) to the 2R,3R/2S,3S (RT=4.47 min.) enantiomeric pair of the free base of the title compound.

The organic layer was concentrated to a volume of 56 liters and a solution of hydrogen chloride (1.2 kg) in isopropanol (6 L) added at 25° C. The title compound precipitated as a solid. This was collected by filtration, washed with ethyl acetate (5 liters) and dried (7.89 kg, 65%), m.p. 126–130° C.

EXAMPLE 2

10.3:1★(2R,3S/2S,3R)-:(2R,3R/2S,3S)-3-(4-Chloro-5-fluoropyrimidin-6-yl)-2-(2,4-difluorophenyl)-1-(1H-1,2,4-triazol-1-yl)butan-2-ol

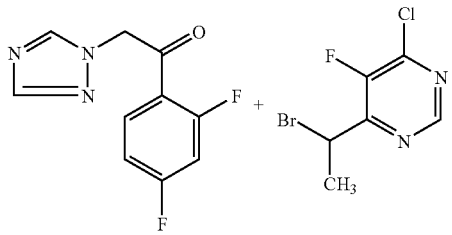

Zn, Pb, I₂, THF

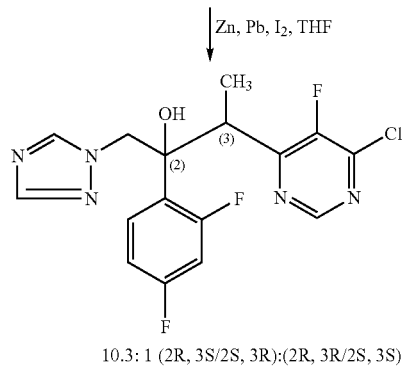

10.3: 1 (2R, 3S/2S, 3R):(2R, 3R/2S, 3S)

(*in situ ratio)

A solution of iodine (2.25 g) in tetrahydrofuran (6 ml) was added dropwise to a stirred slurry of zinc (Britannia Alloys) (3.00 g) and lead (0.15 g) in tetrahydrofuran (19 ml) under a nitrogen atmosphere at 25° C. The reaction temperature was allowed to rise during the addition. The mixture was then cooled to 2° C. A solution of 1-(2,4-difluorophenyl)-2-(1H-1,2,4-triazol-1-yl)ethanone (2.00 g), 6-(1-bromoethyl)-4-chloro-5-fluoropyrimidine (see Preparation 1) (2.84 g) and iodine (0.02 g) in tetrahydrofuran (16 ml) was added dropwise over 10 minutes. The reaction temperature was limited to a maximum of 16° C. during the addition by cooling. Further cooling was then applied to obtain a temperature below +5° C. The reaction was stirred below +5° C. for 30 minutes. A sample of the reaction mixture was taken and subjected to HPLC analysis according to the conditions set out in Example 1. The analysis showed a 10.3:1 molar ratio of the 2R,3S/2S,3R to the 2R,3R/2S,3S enantiomeric pair of the title compound. The yield of the 2R,3S/2S,3R enantiomeric pair was calculated to be 90% using an internal standard.

EXAMPLE 3

11.2:1★(2R,3S/2S,3R)-:(2R,3R/2S,3S)-3-(4-Chloro-5-fluoropyrimidin-6-yl)-2-(2,4-difluorophenyl)-1-(1H-1,2,4-triazol-1-yl)butan-2-ol hydrochloride

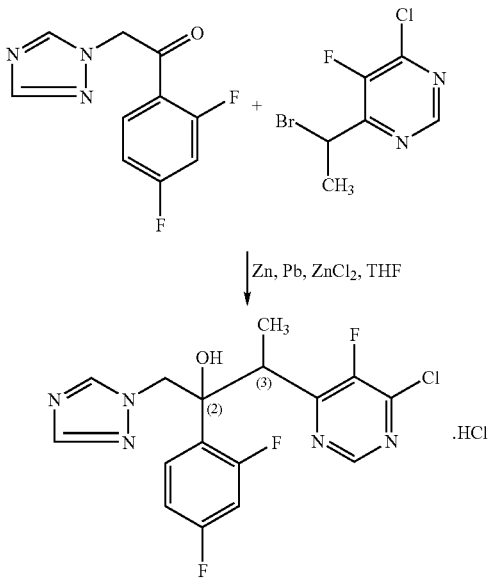

11.2: 1 (2R, 3S/2S, 3R):(2R, 3R/2S, 3S)

(*ratio in isolated product [in situ ratio = 6.7: 1])

Zinc dust (Britannia Alloys) (37.9 g), lead (1.9 g) and zinc chloride (16.2 g) were stirred at 2° C. under an atmosphere of nitrogen in tetrahydrofuran (320 ml). A solution of 1-(2,4-difluorophenyl)-2-(1H-1,2,4-triazol-1-yl)ethanone (26.6 g) and 6-(1-bromoethyl)-4-chloro-5-fluoropyrimidine (see Preparation 1) (40 g) in tetrahydrofuran (215 ml) was added dropwise over 5 minutes. The reaction temperature was kept below 12° C. with applied cooling. The reaction was stirred below +10° C. for 3 hours and at ambient temperature overnight. Completion of the reaction was ascertained by HPLC using the conditions set out in Example 1. The assay showed a 6.7:1 molar ratio of the 2R,3S/2S,3R to the 2R,3R/2S,3S enantiomeric pair of the free base of the title compound. Glacial acetic acid (8 g) and water (400 ml) were then added maintaining the reaction temperature below 25° C. and the mixture stirred for 15 minutes. The solid metal residues were removed by decantation. The mixture was basified to pH 10 using saturated aqueous sodium carbonate solution (600 ml) and adjusted back to pH 8.0 with 5M aqueous hydrochloric acid solution (15 ml). The solids were filtered off and the tetrahydrofuran removed by distillation under reduced pressure. The mixture was extracted with ethyl acetate (2×400 ml). The organic phases were combined and washed with water (400 ml), 2% weight/volume solution of disodium ethylenediaminetetraacetic acid in water (800 ml), followed by water (400 ml). The ethyl acetate layer was concentrated to an oil. The oil was dissolved in ethyl acetate (225 ml) and a 5.75M solution of hydrogen chloride in isopropanol (20 ml) was added. The slurry was granulated at 20° C. for 1 hour and at 0° C. for 1 hour. The crude title compound was isolated by filtration and dried under reduced pressure at 50° C. (39.9 g). HPLC analysis according to the conditions set out in Example 1 showed the proportion of the title compound in the crude product to be 93.9% by weight.

EXAMPLE 4

10.2:1★(2R,3S/2S,3R)-:(2R,3R/2S,3S)-3-(4-Chloro-5-fluoropyrimidin-6yl)-2-(2,4-difluorophenyl)-1-(1H-1,2,4-triazol-1-yl)butan-2-ol

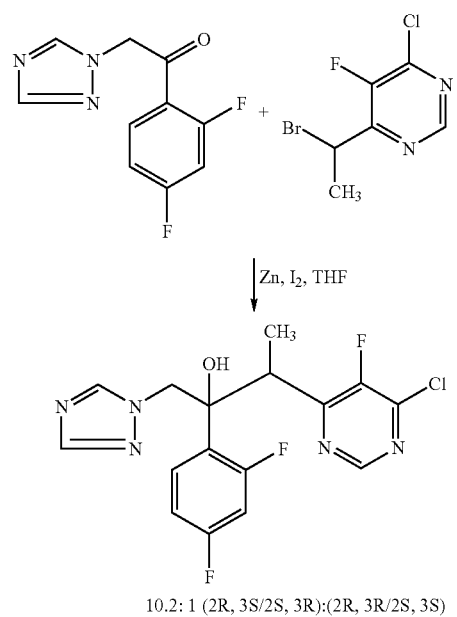

10.2: 1 (2R, 3S/2S, 3R):(2R, 3R/2S, 3S)

(*in situ ratio)

A mixture of zinc dust (Britannia Alloys) (3.00 g) and tetrahydrofuran (20 ml) was stirred overnight at room temperature and then a solution of iodine (2.27 g) in tetrahydrofuran (6 ml) was added, dropwise, over 3 minutes. The temperature of the reaction rose to about 45° C. during the addition and it was cooled to 5–10° C. before the addition of a solution of 1-(2,4-difluorophenyl)-2-(1H-1,2,4-triazol-1-yl)ethanone (2.00 g) and 6-(1-bromoethyl)-4-chloro-5-fluoropyrimidine (see Preparation 1) (2.9 g) in tetrahydrofuran (16 ml) (using the same dropping funnel used for the above iodine addition) over a 40 minute period.

After two hours stirring, a sample of the reaction mixture was taken and subjected to HPLC analysis using the conditions set out in Example 1. By comparison with reference standards (see Example 1), the reaction mixture was shown to contain a 10.2:1 molar ratio of the 2R,3S/2S,3R to the 2R,3R/2S,3S enantiomeric pair of the title compound. The total yield was calculated to be about 72%.

Further examination after one hour showed little deviation from the above position. The reaction was terminated at this point and not further evaluated.

EXAMPLE 5

9.4:1★(2R,3S/2S,3R)-:(2R,3R/2S,3S)-3-(4-Chloro-5-fluoropyrimidin-6yl)-2-(2,4-difluorophenyl)-1-(1H-1,2,4-triazol-1-yl)butan-2-ol

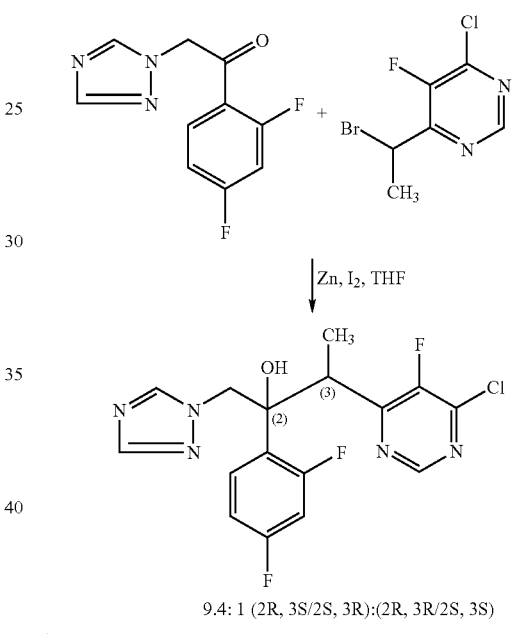

9.4: 1 (2R, 3S/2S, 3R):(2R, 3R/2S, 3S)

(*in situ ratio)

A solution of iodine (2.04 g) in tetrahydrofuran (6 ml) was added dropwise to a stirred slurry of zinc (Brittania Alloys) (3.00 g) in tetrahydrofuran (19 ml) under a nitrogen atmosphere at 25° C. The reaction temperature was allowed to rise during the addition. The mixture was then cooled to 2° C. A solution of 1-(2,4-difluorophenyl)-2-(1H-1,2,4-triazol-1-yl)ethanone (2.00 g), 6-(1-bromoethyl)-4-chloro-5-fluoropyrimidine (see Preparation 1) (3.00 g) and iodine (0.23 g) in tetrahydrofuran (16 ml) was added dropwise over 10 minutes, maintaining the temperature below +5° C. with applied cooling. The reaction was stirred below +5° C. for 30 minutes. A sample of the reaction mixture was taken and subjected to HPLC analysis according to the conditions set out in Example 1. The analysis showed a 9.4:1 molar ratio of the 2R,3S/2S,3R to the 2R,3R/2S,3S enantiomeric pair of the title compound. The yield of the 2R,3S/2S,3R enantiomeric pair was calculated to be 77% using an internal standard.

EXAMPLE 6

10.2:1★ (2R,3S/2S,3R)-:(2R,3R/2S,3S)-3-(4-Chloro-5-fluoropyrimidin-6-yl)-2-(2,4-difluorophenyl)-1-(1H-1,2,4-triazol-1-yl)butan-2-ol

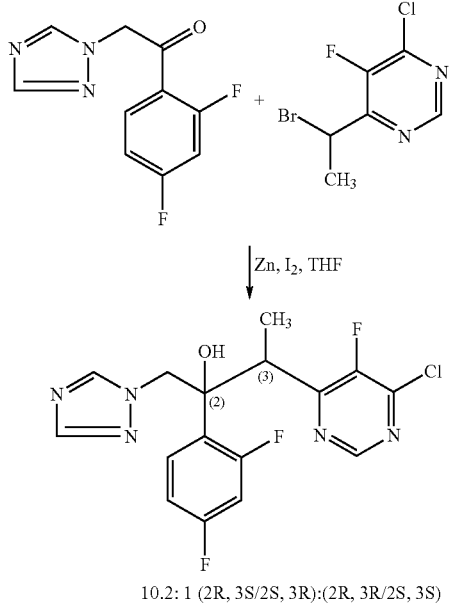

10.2: 1 (2R, 3S/2S, 3R):(2R, 3R/2S, 3S)

(*in situ ratio)

A solution of iodine (2.20 g) in tetrahydrofuran (6 ml) was added dropwise to a stirred slurry of zinc (Britannia Alloys) (3.00 g) in tetrahydrofuran (19 ml) under a nitrogen atmosphere at 25° C. The reaction temperature was allowed to rise during the addition. The mixture was then cooled to 2° C. A solution of 1-(2,4-difluorophenyl)-2-(1H-1,2,4-triazol-1-yl)ethanone (2.00 g) and 6-(1-bromoethyl)-4-chloro-5-fluoropyrimidine (see Preparation 1) (2.84 g) in tetrahydrofuran (16 ml) was added dropwise over 10 minutes. During the first 2 minutes of this addition a solution of iodine (0.07 g) in tetrahydrofuran (4 ml) was also added. Cooling was applied to maintain the reaction temperature below +5° C. The reaction was stirred below +5° C. for 30 minutes. A sample of the reaction mixture was taken and subjected to HPLC analysis according to the conditions set out in Example 1. The analysis showed a 10.2:1 molar ratio of the 2R,3S/2S,3R to the 2R,3R/2S,3S enantiomeric pair of the title compound. The yield of the 2R,3S/2S,3R enantiomeric pair was calculated to be 87% using an internal standard.

EXAMPLE 7

64:1★(2R,3S/2S,3R)-:(2R,3R/2S,3S)-3-(4-Chloro-5-fluoropyrimidin-6-yl)-2-(2,4-difluorophenyl)-1-(1H-1,2,4-triazol-1-yl)butan-2-ol hydrochloride

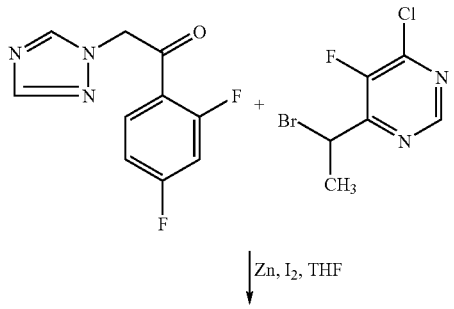

-continued

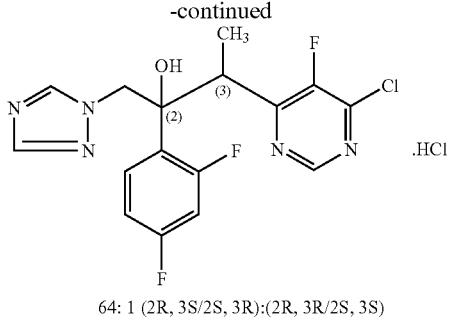

64: 1 (2R, 3S/2S, 3R):(2R, 3R/2S, 3S)

(*ratio in isolated product)

A solution of iodine (20.52 g) in tetrahydrofuran (65 ml) was added dropwise to a stirred slurry of zinc dust (28.6 g) in tetrahydrofuran (160 ml) under a nitrogen atmosphere at 20° C. The reaction temperature was allowed to rise to 25° C. The mixture was then cooled to from 0° C. to 5° C. A solution of 1-(2,4-difluorophenyl)-2-(1H-1,2,4-triazol-1-yl)ethanone (20.0 g), 6-(1-bromoethyl)-4-chloro-5-fluoropyrimidine (see Preparation 1) (23.6 g) and iodine (2.28 g) in tetrahydrofuran (160 ml) was added dropwise over 75 minutes, maintaining a reaction temperature of from 0° C. to +5° C. with applied cooling. The reaction was stirred below +5° C. for 30 minutes. Completion of the reaction was ascertained by HPLC using the conditions set out in Example 1. The assay showed the stoichiometric yield of the 2R,3S/2S,3R enantiomeric pair to be 88%. Glacial acetic acid (5.4 ml) and water (260 ml) were then added maintaining the temperature below 25° C. The solid metal residues were removed by decantation. The mixture was basified to pH 10 using saturated aqueous sodium carbonate solution (180 ml) and then adjusted to pH 8.0 with 5M aqueous hydrochloric acid solution. The solids were filtered off and the tetrahydrofuran removed by distillation under reduced pressure. Ethyl acetate (260 ml) was added and the mixture stirred for 10 minutes. The organic layer was separated and the aqueous phase was extracted with ethyl acetate (86 ml). The organic phases were combined and washed with a 2% weight/volume solution of disodium ethylenediaminetetraacetic acid in water (286 ml), water (139 ml) and saturated brine (52 ml). The ethyl acetate layer was concentrated to a volume of 150 ml. A solution of sulphosalicyclic acid (1.86 g) in isopropanol (5 ml) was added and the slurry granulated at 20° C. for 2 hours. The solid was filtered off and washed with ethyl acetate (2×3 ml). A 6M solution of hydrogen chloride in isopropanol (1.1 molar ratio relative to the amount of product and 1-(2,4-difluorophenyl)-2-(1H-1,2,4-triazol-1-yl)ethanone in the filtrate) was added to the filtrate and the slurry granulated at 25° C. for 2 hours and at from 0 to 2° C. for a further hour. The crude title compound was isolated by filtration, washed with ethyl acetate (20 ml) and dried under reduced pressure at 50° C. The mass yield was 30 g. HPLC analysis according to the conditions set out in Example 1 showed the product to contain a 75.7% by weight stoichiometric yield of the 2R,3S/2S,3R enantiomeric pair of the title compound.

EXAMPLE 8

5.5:1★ (2R,3S/2S,3R)-:(2R,3R/2S,3S)-3-(2,4-Dichloro-5-fluoropyrimidin-6-yl)-2-(2,4-difluorophenyl)-1-(1H-1,2,4-triazol-1-yl)butan-2-ol

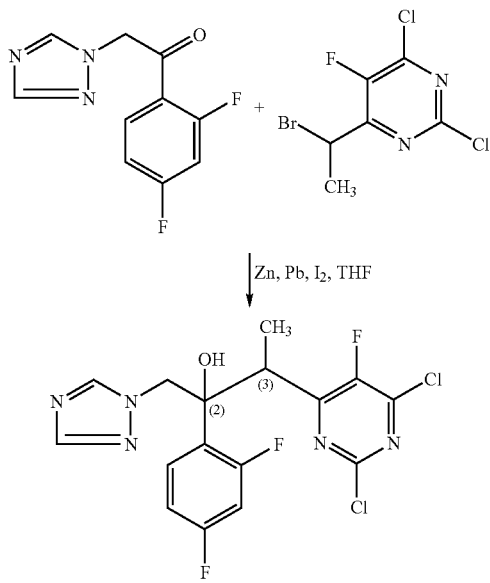

5.5: 1 (2R, 3S/2S, 3R):(2R, 3R/2S, 3S)

(*ratio in isolated product)

A stirred mixture of zinc powder (Britannia Alloys) (78.6 g), lead powder (Aldrich) (3.9 g) and tetrahydrofuran (450 ml) was kept at 20° C. for 17 hours then treated with a solution of iodine (153 g) in tetrahydrofuran (450 ml), keeping the temperature below 45° C. using cooling. The mixture was then cooled to −30° C. and a solution of 1-(2,4-difluorophenyl)-2-(1H-1,2,4-triazol-1-yl)ethanone (134.7 g) and 6-(1-bromoethyl)-2,4-dichloro-5-fluoropyrimidine (see Preparation 3) (82.4 g) in tetrahydrofuran (300 ml) added, keeping the temperature between −3 and −5° C. The mixture was warmed to 30° C. and kept at this temperature for 2 hours, then quenched with glacial acetic acid (150 ml) and water (750 ml). The supernatant liquor was decanted from the metal residues and the tetrahydrofuran removed by concentration under reduced pressure. Ethyl acetate (2.5 L) was added and the mixture basified by adding saturated aqueous sodium carbonate solution (1.5 L). The mixture was granulated at 20° C. for 30 minutes and the precipitated zinc carbonate removed by filtration. The organic layer in the filtrate was separated, washed with water (2×2.0 L) and concentrated under reduced pressure. The solution obtained was treated with a solution of 5-sulfosalicylic acid dihydrate (107.5 g) in isopropanol (215 ml). After granulating for 1 hour at 20° C., the precipitated 1-(2,4-difluorophenyl)-2-(1H-1,2,4-triazol-1-yl)ethanone sulfosalicylate was removed by filtration. The filtrate was washed with 5% w/v aqueous disodium ethylenediaminetetracetate dihydrate solution (2×500 ml), water (500 ml) and then concentrated under reduced pressure to give the crude product as a syrup (123.8 g).

HPLC analysis using the conditions set out in Example 1 showed the product to contain a 5.5:1 molar ratio of the 2R,3S/2S,3R (RT=7.1 min.) to the 2R,3R/2S,3S (RT=5.6 min.) enantiomeric pair of the title compound.

$^{1}$H-NMR (300 MHz, CDCl$_{3}$): δ=1.06 (d, 3H), 3.95 (q, 1H), 4.34 (d, 1H), 4.70 (d, 1H), 5.55 (s,br., 1H), 6.65–6.80 (m, 2H), 7.45–7.56 (m, 1H), 7.55 (s, 1H), 7.93 (s, 1H) ppm.

EXAMPLE 9

9.2:1★(2R,3S/2S,3R)-:(2R,3R/2S,3S)-3-(1-Benzyl-5-fluoropyrimidin-6-on-4-yl)-2-(2,4-difluorophenyl)-1-(1H-1,2,4-triazol-1-yl)butan-2-ol

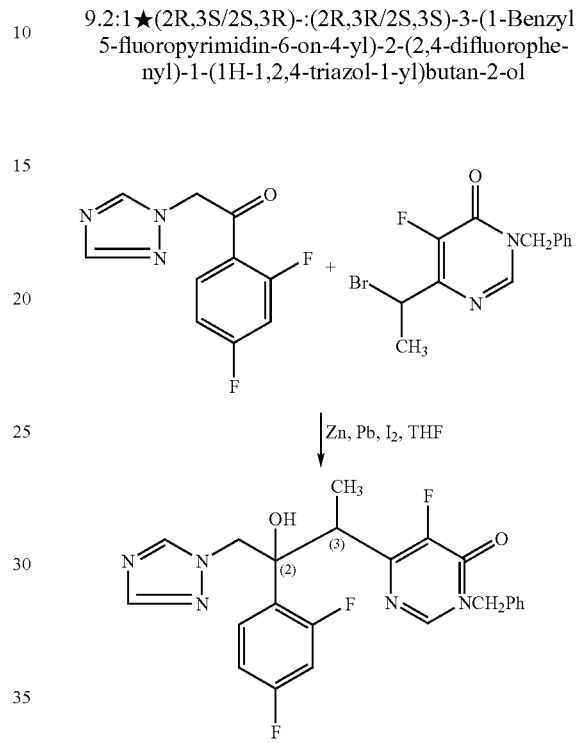

9.2: 1 (2R, 3S/2S, 3R):(2R, 3R/2S, 3S)

(*ratio in isolated product)

A stirred mixture of zinc dust (Pasminco) (573 mg), lead powder (29 mg) and tetrahydrofuran (6 ml) was kept at room temperature for 18 hours and then a solution of iodine (370 mg) in tetrahydrofuran (2 ml) was added. A solution of 1-(2,4-difluorophenyl)-2-(1H-1,2,4-triazol-1-yl)ethanone (653 mg) and 1-benzyl-4-(1-bromoethyl)-5-fluoropyrimidin-6-one (see Preparation 5) (1.00 g) in tetrahydrofuran (7 ml) was then added, dropwise, to the mixture over 10 minutes. The reaction was heated to about 40° C. for 1 hour then cooled and quenched with glacial acetic acid (1 ml) and water (10 ml). The mixture was partitioned between water and ethyl acetate, the organic layer separated and washed with an aqueous solution of potassium bicarbonate followed by brine, then dried (MgSO$_{4}$) and concentrated under reduced pressure. The residue was chromatographed on silica gel eluting with hexane:ethyl acetate (solvent gradient of 4:1 to 1:1 to 0:1, by volume, used) to provide the product as a white solid (519 mg, 39%).

HPLC analysis using the conditions set out in Example 1 showed the product to contain a 9.2:1 molar ratio of the 2R,3S/2S,3R (RT=3.78 min.) to the 2R,3R/2S,3S (RT=5.28 min.) enantiomeric pair of the title compound.

$^{1}$H-NMR (300 MHz, CDCl$_{3}$): δ=1.02 (d, 3H), 3.91 (q, 1H), 4.30 (d, 1H), 4.78 (d, 1H), 5.12 (d, 1H), 5.19 (d, 1H), 5.95 (s, 1H), 6.72–6.86 (m, 2H), 7.30–7.56 (m, 7H), 7.89 (s, 1H), 8.00 (s, 1H) ppm.

EXAMPLE 10

12.5:1★(2R,3S/2S,3R)-:(2R,3R/2S,3S)-3-(4-chloro-pyrimidin-6-yl)-2-(2,4-difluorophenyl)-1-(1H-1,2,4-triazol-1-yl)butan-2-ol

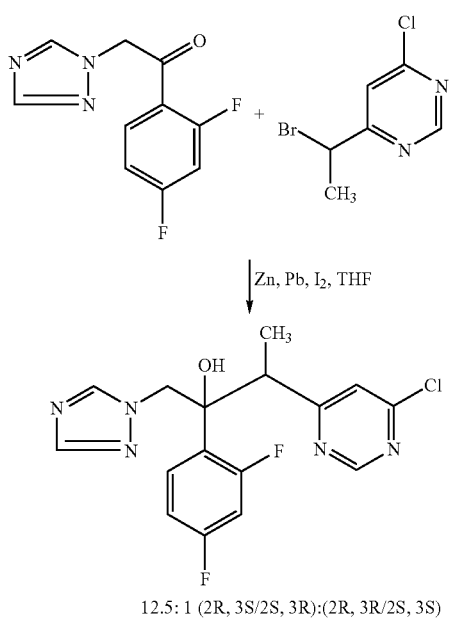

12.5: 1 (2R, 3S/2S, 3R):(2R, 3R/2S, 3S)

(*in situ ratio)

A mixture of zinc dust (Britannia Alloys) (249 g), lead powder (12.3 g) and tetrahydrofuran (760 ml) was stirred overnight at room temperature and then a solution of iodine (203.4 g) in tetrahydrofuran (650 ml) was added, dropwise. The temperature of the reaction rose to about 45° C. during the addition. It was then cooled to 5–10° C. and a solution of 1-(2,4-difluorophenyl)-2-(1H-1,2,4-triazol-1-yl)ethanone (199 g), 4-(1-bromoethyl)-6-chloropyrimidine (293 g of the crude product of Preparation 6: calculated to contain 217 g of this pyrimidine) and iodine (22.6 g) in tetrahydrofuran (1600 ml) was added over 30 minutes keeping the temperature below 55° C. After 1 hour, a sample of the reaction mixture was taken and subjected to HPLC analysis using the conditions set out in Example 1. The molar ratio of the 2R,3S/2S,3R (retention time 4.23 minutes) to the 2R,3R/2S,3S (retention time 3.4 minutes) enantiomeric pair was determined to be 12.5:1.

The reaction was cooled to 20° C. and quenched by the addition of glacial acetic acid (56 g) and water (180 ml). The zinc residues were removed by filtration and the solution treated with aqueous sodium carbonate solution until the mixture reached pH 10. The pH was then lowered to 7.5 using dilute aqueous hydrochloric acid solution and the zinc carbonate precipitated was removed by filtration. The solution was concentrated under reduced pressure to remove most of the tetrahydrofuran solvent to provide an aqueous slurry that was extracted using dichloromethane (2×500 ml). The organic phases were combined and washed with 5% w/w aqueous ethylenediaminetetraacetic acid, disodium salt solution (2×500 ml). After concentrating the organic phase under reduced pressure, the residue was crystallised from isopropyl alcohol (2.5 liters) and the solid collected by filtration. After drying at 50° C. under reduced pressure, the product (140 g) was analysed by HPLC and shown to contain 91% by weight of the (2R,3S/2S,3R) enantiomeric pair of the title compound.

$^1$H-NMR (300 MHz, CDCl$_3$): δ=1.1 (d,3H), 3.65 (q, 1H), 4.15 (d, 1H), 4.8 (d, 1H), 6.15 (s, 1H), 6.8 (m, 2H), 7.5 (s, 1H), 7.55 (m, 1H), 7.65 (s, 1H), 7.9 (s, 1H), 8.9 (s, 1H) ppm.

The following Preparations illustrate the preparation of certain starting materials used in the preceding Examples together with the further processing of certain compounds of these Examples:—

PREPARATION 1

6-(1-Bromoethyl)-4-chloro-5-fluoropyrimidine

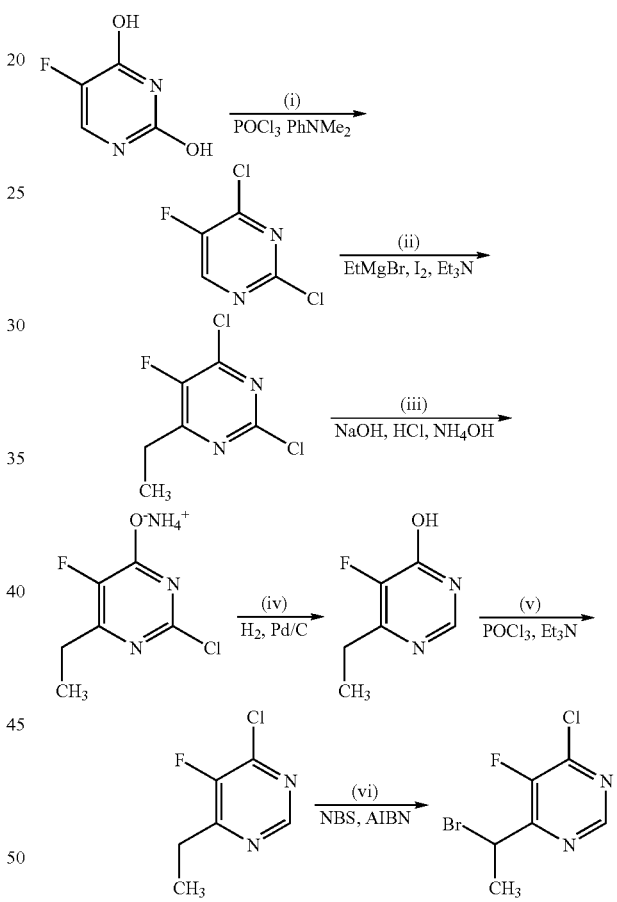

(i) 2,4-Dichloro-5-fluoropyrimidine

A stirred mixture of 5-fluorouracil (111.5 kg) and phosphorus oxychloride (394.6 kg) was heated to 95° C. and N,N-dimethylaniline (207 kg) added over 1 hour during which time an exotherm was noted. The mixture was maintained at 95° C. for 15 hours then cooled to room temperature and cautiously quenched into ice-cooled 3N aqueous hydrochloric acid solution (450 L) over 4 hours, maintaining the temperature below 30° C. during this operation. The mixture was extracted with dichloromethane (2×390 L), the combined extracts washed with water (280 L) until the aqueous washings reached pH7 and concentrated under reduced pressure. The residue taken up in dimethoxyethane (190 L) and the solution of the product used directly in the next step.

$^1$H-NMR (300 MHz, CDCl$_3$): δ=8.5 (s, 1H) ppm.

(ii) 2,4-Dichloro-6-ethyl-5-fluoropyrimidine

To a stirred mixture of magnesium turnings (12.1 kg) in tetrahydrofuran (161 L) was added a solution of bromoethane (54.3 kg) in tetrahydrofuran (53 L) maintaining the reaction temperature below 50° C. during the addition. The solution of the Grignard reagent was cooled to 0° C. and a solution of the compound of part (i) (56 kg) in dimethoxyethane (170 L) added, maintaining the reaction temperature below 15° C. during the addition. The reaction was stirred for 1 hour at 15° C. and cooled to 0° C. A solution of triethylamine (34 kg) in tetrahydrofuran (70 L) was added, maintaining the reaction temperature at about 5° C., followed by a solution of iodine (85 kg) in tetrahydrofuran (256 L), maintaining the reaction temperature below 15° C. The reaction was then quenched with water (840 L), maintaining the reaction temperature below 25° C. The pH was adjusted to 1 using 5N aqueous hydrochloric acid solution (50 L) and the mixture extracted with toluene (1×490 L followed by 1×210 L). The combined organic layers were washed with 2% w/w aqueous sodium metabisulphite solution (700 L) then water (700 L) added and the remaining tetrahydrofuran removed by distillation under reduced pressure. The mixture was cooled, the organic layer separated, washed with water (425 L) and then concentrated under reduced pressure to provide the product as an oil (50 kg).

(iii) 2-Chloro-6-ethyl-5-fluoro-4-hydroxypyrimidine, ammonium salt

A mixture of the compound of part (ii) (40 kg) and water (10 kg) was heated to 90° C. and 4N aqueous sodium hydroxide solution (127 L) added. Heating was continued at 80° C. for 30 minutes and then the mixture was cooled to 25° C. The mixture was washed with toluene (124 L), the aqueous layer separated and dichloromethane (162 L) added thereto. To this mixture was added concentrated hydrochloric acid until pH1 was achieved. The organic layer was separated and the aqueous layer extracted with dichloromethane (162 L). The combined organic layers were treated with activated carbon (Norit-trade mark) (8.8 kg). The solution was filtered and the filtrate treated with concentrated aqueous ammonia solution until pH9 was achieved. The product precipitated as a solid and was collected by filtration (34 kg), m.p. 125–131° C.

(iv) 6-Ethyl-5-fluoro-4-hydroxypyrimidine

To a mixture of the compound of part (iii) (34 kg), ethanol (170 L) and water (5 kg) was added 5% w/w palladium-on-carbon (50% w/w water content) (3.4 kg) and the mixture hydrogenated at 50° C. and 345 kPa (50 psi) until completion of the reaction. Water (10.5 L) was added and the catalyst removed by filtration. The filtrate was concentrated under reduced pressure to a small volume and extracted with dichloromethane (2×58 L). The combined organic extracts were concentrated under reduced pressure and toluene (150 L) added. The mixture was concentrated under reduced pressure to 50 L in volume, toluene (50 L) added and cooled to 4° C. for 4 hours. The precipitated product was collected by filtration, washed with toluene (10 L) and dried (Yield=20 kg), m.p. 112–4° C.

$^1$H-NMR (300 MHz, CDCl$_3$): δ=1.25 (m, 3H), 2.73 (m, 2H), 8.00 (s, 1H) ppm.

(v) 4-Chloro-6-ethyl-5-fluoropyrimidine

To a mixture of the compound of part (iv) (40 kg), dichloromethane (120 L) and triethylamine (28.4 g) was slowly added phosphorus oxychloride (47.2 kg) over 3 hours maintaining the reaction temperature below 40° C. during the addition. The mixture was heated under reflux for 5 hours, cooled to 25° C. and cautiously quenched into 3N aqueous hydrochloric acid solution (176 L), maintaining the temperature below 20° C. during this operation. The layers were separated, the aqueous phase extracted with dichloromethane (50 L) and the combined organic layers washed with water (50 L). The organic layer was concentrated under reduced pressure to provide the product as an oil (40.69 kg).

$^1$H-NMR (300 MHz, CDCl$_3$): δ=1.30 (t, 3H), 2.87 (q, 2H), 8.65 (s, 1H) ppm.

(vi) 6-(1-Bromoethyl)-4-chloro-5-fluoropyrimidine

A stirred mixture of the compound of part (v) (38.5 kg), azoisobutyronitrile (AIBN) (1.92 kg), N-bromosuccinimide (49 kg) and dichloromethane (198 L) was heated under reflux under nitrogen for 12 hours. The mixture was cooled to 25° C. and water (239 L) added. The layers were separated and the aqueous layer extracted with dichloromethane (120 L). The combined organic layers were washed with a solution of sodium metabisulphite (22.8 kg) in water (239 L), followed by water (239 L). The organic layer was concentrated under reduced pressure, toluene (240 L) was added and the resulting solution concentrated under reduced pressure to give the product as an oil (61.7 kg).

$^1$H-NMR (300 MHz, CDCl$_3$): δ=2.08 (d, 3H), 5.35 (q, 1H), 8.80 (s, 1H) ppm.

PREPARATION 2

(2R,3S)-2-(2,4-Difluorophenyl)-3-(5-fluoropyrimidin-4-yl)-1-(1H-1,2,4-triazol-1-yl)butan-2-ol

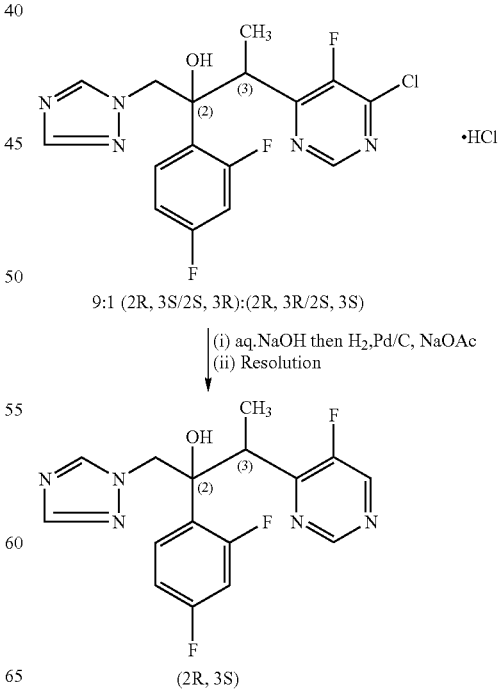

9:1 (2R, 3S/2S, 3R):(2R, 3R/2S, 3S)

(i) aq.NaOH then H$_2$,Pd/C, NaOAc
(ii) Resolution (2R, 3S)

(i) (2R,3S/2S,3R)-2-(2,4-Difluorophenyl)-3-(5-fluoropyrimidin-4-yl)-1-(1H-1,2,4-triazol-1-yl)butan-2-ol A stirred mixture of the product obtained by the procedure of Example 1 (26.5 kg), dichloromethane (400 L) and water (184 L) was adjusted to pH11 using 40% w/w aqueous sodium hydroxide solution (10 L). The organic layer was separated, washed with a solution of disodium ethylenediaminetetracetate dihydrate (8.74 kg) in water (183.5 L) followed by water (184 L) and then concentrated under reduced pressure to an oil. This was dissolved in ethanol (134 L), sodium acetate (8 kg) and 5% w/w palladium-on-carbon (50% w/w water content) (3.34 kg) added and the mixture hydrogenated at 103 kPa (15 psi) and 25° C. until completion of the reaction. The catalyst was removed by filtration and the filtrate concentrated to a volume of 51 liters. Dichloromethane (152 L) and water (152 L) were added and the pH adjusted to 11 using 40% w/w aqueous sodium hydroxide solution. The layers were separated and the aqueous layer extracted with dichloromethane (61 L). The combined organic extracts were washed with water (61 L), concentrated under reduced pressure, isopropanol (70 L) added and concentrated to a volume of 62 L. The mixture was granulated for 3 hours at 20° C., collected by filtration, washed with isopropanol (2×5 L) and dried to provide the title compound as the major enantiomeric pair in the product (19 kg), m.p. 127° C.

(ii) (2R,3S)-2-(2,4-Difluorophenyl)-3-(5-fluoropyrimidin-4-yl)-1-(1H-1,2,4-triazol-1-yl)butan-2-ol To a solution of the compound of part (i) (18.93 kg) in acetone (426 L) was added a solution of R-(−)-10-camphorsulphonic acid (12.57 kg) in methanol (142 L) and the mixture heated under reflux until a homogenous solution was obtained. The solution was cooled to 20° C. and granulated overnight. The solid was collected by filtration, washed with acetone (9.35 kg) and dried to provide (2R,3S)-2-(2,4-difluorophenyl)-3-(5-fluoropyrimidin-4-yl)-1-(1H-1,2,4-triazol-1-yl)butan-2-ol R-(−)-10-camphorsulphonate as a white solid (12.3 kg).

The above camphorsulphonate salt (12.3 kg) was taken up in dichloromethane (61.5 L) and water (61.5 L) and the pH adjusted to 11 by adding 40% w/w aqueous sodium hydroxide solution (2.5 L). The layers were separated and the aqueous layer extracted with dichloromethane (14 L). The combined organic extracts were washed with water (3×45 L), filtered and the solvent removed by distillation under reduced pressure. Isopropanol (30 L) was added and the distillation continued until a volume of 22 liters was achieved. The mixture was cooled to 0° C. and granulated for 2 hours. The product was collected by filtration and washed with isopropanol (2×4 L) to provide the title compound as a white solid (7.6 kg).

PREPARATION 3

6-(1-Bromoethyl)-2,4-dichloro-5-fluoropyrimidine

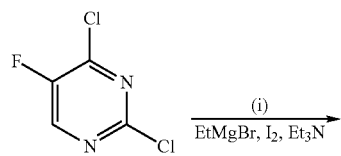

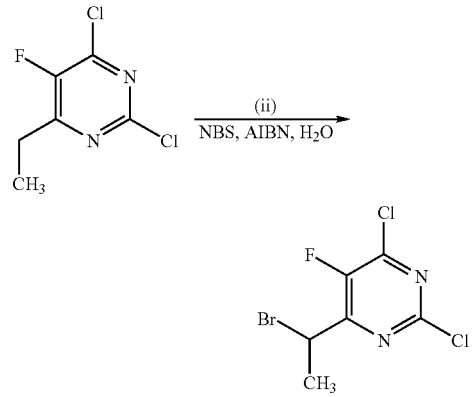

(i) 2,4-Dichloro-6-ethyl-5-fluoropyrimidine

To a stirred mixture of magnesium turnings (90.4 g) in tetrahydrofuran (1.04 L) was added a solution of bromoethane (407 g) in tetrahydrofuran (1.04 L), maintaining the reaction temperature between 35–40° C. The solution of the Grignard reagent was stirred for 30 minutes at 20° C., cooled to 0° C. and a solution of the compound of Preparation 1 (i) (420 g) in dimethoxyethane (600 ml) was added keeping the reaction temperature below 15° C. The mixture was stirred for 1 hour at 15° C. then cooled to 0° C. A solution of triethylamine (254 g) in tetrahydrofuran (510 ml) was added at 5° C., followed by a solution of iodine (632 g) in tetrahydrofuran (1.92 L), keeping the temperature below 15° C. The reaction was quenched with water (6 L) keeping the temperature below 25° C. The mixture was acidified to pH1 with 5N aqueous hydrochloric acid solution and extracted with ethyl acetate (2×6 L). The combined organic extracts were washed with a 10% w/v aqueous sodium metabisulphite solution (12 L). Water (4 L) was added and most of the organic solvent removed by evaporation under reduced pressure. The layers were separated and the aqueous layer extracted with ethyl acetate (2 L). The combined organic extracts were treated with glacial acetic acid (400 ml) and concentrated under reduced pressure at 80° C. The mixture was cooled to 20° C. and the oil partitioned between dichloromethane (3 L) and 1N aqueous sodium hydroxide solution (3 L). The organic layer was separated, washed with water (3.0 L) and concentrated under reduced pressure to provide the product as an oil (402 g).

$^1$H-NMR (300 MHz, CDCl$_3$): δ=1.33 (t, 3H), 2.87 (dq, 2H) ppm.

(ii) 6-(1-Bromoethyl)-2,4-dichloro-5-fluoropyrimidine

A mixture of the compound of part (i) (400 g), N-bromosuccinimide (730 g), azoisobutyronitrile (33.7 g), bromine (65.5 g) and water (6.4 L) was heated at 80–85° C. for 5 hours. Further N-bromosuccinimide (183 g) was added, heating continued for 2 hours then further azoisobutyronitrile (33.7 g) added. After heating for 2 hours at 85° C. further azoisobutyronitrile (33.7 g) was added and heating continued for 3 hours. The reaction was cooled, diluted with water (4 L) and extracted with dichloromethane (2×3 L). The combined organic extracts were washed with a solution of sodium metabisulphate (600 g) in water (2.5 L), followed by water (3 L). The solvent was removed by evaporation under reduced pressure, toluene (1.0 L) added and the solution concentrated under reduced pressure to give the product as an oil (534 g).

¹H-NMR (300 MHz, CDCl₃): δ=2.05 (d, 3H), 5.06 (q, 1H) ppm.

PREPARATION 4

(2R,3S)-2-(2,4-Difluorophenyl)-3-(5-fluoropyrimidin-4-yl)-1-(1H-1,2,4-triazol-1-yl)butan-2-ol

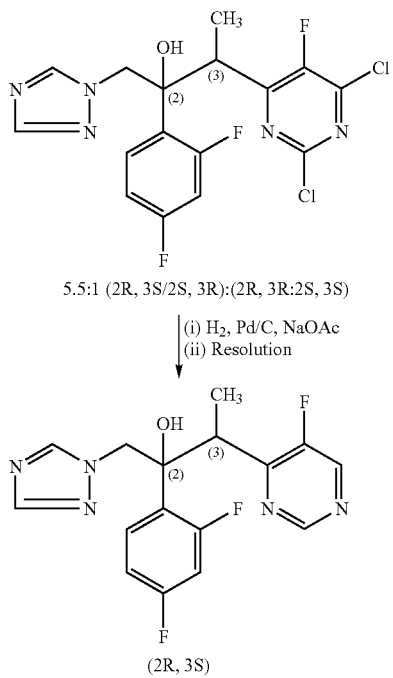

5.5:1 (2R, 3S/2S, 3R):(2R, 3R:2S, 3S)

(i) H₂, Pd/C, NaOAc
(ii) Resolution (2R, 3S)

(i) (2R,3S/2S,3R)-2-(2,4-Difluorophenyl)-3-(5-fluoropyrimidin-4-yl)-1-(1H-1,2,4-triazol-1-yl)butan-2-ol A stirred mixture of the product obtained by the procedure of Example 8 (123.8 g), sodium acetate (27.4 g), 5% w/w palladium-on-carbon (50% w/w water content) (18.6 g) and ethanol (1.24 L) was hydrogenated at 50° C. and 345 kPa (50 psi) for 19 hours. The reaction was cooled to 25° C. and the catalyst filtered off and washed with ethanol (100 ml). The filtrate was concentrated under reduced pressure to dryness and the residue partitioned between dichloromethane (1.0 L) and 10% w/v aqueous potassium bicarbonate solution (1.0 L). The organic layer was separated and washed with water, then evaporated under reduced pressure to dryness to provide the title compound as the major enantiomeric pair in the product. This was used directly in the next step.

¹H-NMR (300 MHz, d₆-DMSO): δ=1.10 (d, 3H), 3.90 (q, H), 4.33 (d, 1H), 4.80 (d, 1H), 6.87–6.93 (m, 1H), 7.10–7.20 (m, 1H), 7.21–7.34 (m, 1H), 7.60 (s, 1H), 8.21 (s, 1H), 8.82 (s, 1H), 9.02 (s, 1H) ppm.

(ii) (2R,3S)-2-(2,4-Difluorophenyl)-3-(5-fluoropyrimidin-4-yl)-1-(1H-1,2,4-triazol-1-yl)butan-2-ol The product of part (i) was taken up in acetone (383 ml) and a solution of R-(−)-camphor-10-sulphonic acid (42.1 g) in acetone (300 ml) added. The mixture was granulated at 20° C. for 18 hours and then cooled to 0° C. for 1 hour. The solid was filtered off and washed with cold acetone (100 ml) then dried to provide a crude camphorsulphonate product (35.4 g).

HPLC analysis (25 cm×4.6 mm C18 Dynamax 60 angstrom reverse phase column, mobile phase=65:35, by volume, acetonitrile:water, flow rate 1 ml/min.) showed this material to be 91% chemically pure and to contain a 63:37 molar ratio of the 2R,3S- to the 2S,3R-enantiomeric pair.

This partially resolved salt (34 g) was dissolved in a mixture of methanol (110 ml) and acetone (329 ml) which was heated under reflux. The solution was cooled to 20° C. slowly and granulated overnight. The solid was collected by filtration, washed with acetone (50 ml) and dried to provide (2R,3S)-2-(2,4-difluorophenyl)-3-(5-fluoropyrimidin-4-yl)-1-(1H-1,2,4-triazol-1-yl)butan-2-ol R-(−)-camphor-10-sulphonate as white crystals (17.1 g), m.p. 187° C.

HPLC analysis showed this material to be 100% optically pure.

This salt (17 g) was partitioned between dichloromethane (85 ml) and water (85 ml) and the pH adjusted to 11 by adding 40% w/w aqueous sodium hydroxide solution. The layers were separated and the aqueous phase extracted with dichloromethane (20 ml). The combined organic extracts were washed with water (2×80 ml), filtered and the solvent removed by evaporation under reduced pressure. Isopropanol (26 ml) was added, the solution cooled to 0° C. and granulated for 1 hour. The solid was collected by filtration, washed with cold isopropanol (5 ml) and dried under reduced pressure at 50° C. to provide the product (8.4 g), m.p. 133° C.

¹H-NMR (300 MHz, d₆-DMSO): δ=1.10 (d, 3H), 3.90 (q, 1H), 4.33 (d, 1H), 4.80 (d, 1H), 6.87–6.93 (m, 1H), 7.10–7.20 (m, 1H), 7.21–7.34 (m, 1H), 7.60 (s, 1H), 8.21 (s, 1H), 8.82 (s, 1H), 9.02 (s, 1H) ppm.

PREPARATION 5

1-Benzyl-4-(1-bromoethyl)-5-fluoropyrimidin-6-one

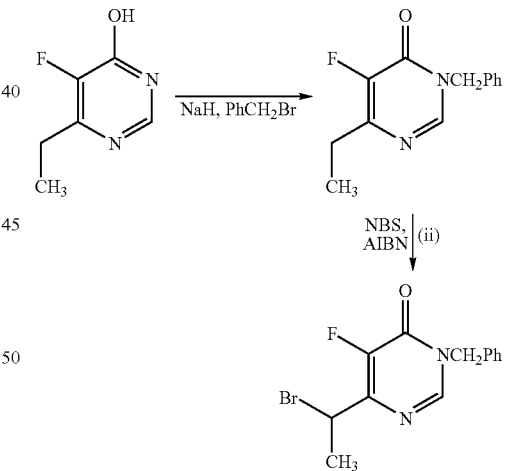

(i) 1-Benzyl-4-ethyl-5-fluoropyrimidin-6-one

Sodium hydride (60% w/w dispersion in oil, 928 mg) was triturated with hexane then dimethylformamide (30 ml) added. To this mixture was added the compound of Preparation 1 (iv) (3 g) and, following cessation of the effervescence, benzyl bromide (2.51 ml). The mixture was stirred for 1 hour then quenched with water. The mixture was partitioned between diethyl ether and water, the ether layer separated and washed successively with dilute sodium hydroxide solution, brine and water, then concentrated under reduced pressure to provide the required product as white crystals (4.04 g). LRMS m/z=232.9(m)+.

¹H-NMR (300 MHz, CDCl₃): δ=1.22 (t, 3H), 2.63 (dq, 2H), 5.14 (s, 2H), 7.32–7.40 (m, 5H), 7.93 (s, 1H) ppm.

(ii) 1-Benzyl-4-(1-bromoethyl)-5-fluoropyrimid-6-one

A mixture of the compound of Preparation 5(i) (2 g), N-bromosuccinimide (1.76 g), azoisobutyronitrile (71 mg) and dichloromethane (20 ml) was heated under reflux under nitrogen for 20 hours. The reaction was cooled, washed successively with a dilute aqueous solution of sodium metabisulphite, water and then brine, then dried (MgSO₄) and concentrated under reduced pressure. The residue was chromatographed on silica gel eluting with ethyl acetate:hexane (1:7, by volume) to provide the product as a white syrup (1.60 g). LRMS m/z=310.9/312.9(m)+.

¹H-NMR (300 MHz, CDCl₃): δ=1.94 (d, 3H), 5.07 (d, 1H), 5.17 (d, 1H), 5.30 (q, 1H), 7.30–7.41 (m, 5H), 8.00 (s, 1H) ppm.

PREPARATION 6

4-(1-Bromoethyl)-6-chloropyrimidine

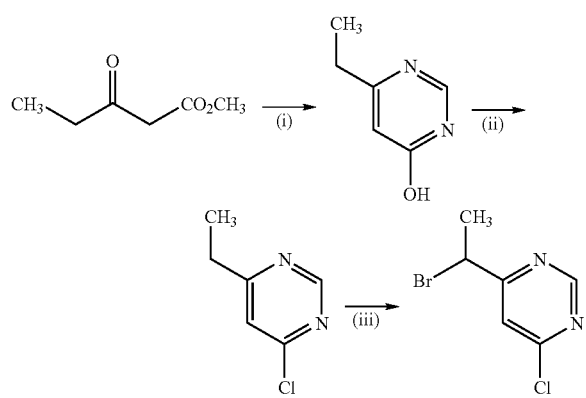

(i) 4-Ethyl-6-hydroxypyrimidine

Formamidine acetate (500 g) and methyl 3-oxopentanoate (500 g) were added to a solution of sodium methoxide (500 g) in methanol (4 L) at 20° C. and the mixture stirred for 15 hours. Water (1 L) and acetic acid (500 ml) were added to give a pH of 7. The solvent was removed by evaporation under reduced pressure and the aqueous residue was diluted with water (1 L) and extracted with methyl ethyl ketone (4×2.5 L). The organic phases were combined and concentrated by evaporation under reduced pressure to give an orange syrup. The syrup was dissolved in ethyl acetate (1 L) and the solution stirred for 15 hours to give a solid. The solid was collected by filtration, washed with ethyl acetate (200 ml, at 10° C.) and dried at 50° C. under reduced pressure to provide the title compound (183 g). After concentrating the mother liquors under reduced pressure, diethyl ether (3 L) was added to provide a solid. This was solid was collected by filtration, washed with tert-butyl methyl ether (200 ml) and dried at 50° C. under reduced pressure to provide a second crop of the title compound (195 g). The total yield of the title compound was approximately 79%.

¹H-NMR (300 MHz. D₂O): δ=1.02–1.12 (m, 3H), 1.89 (s, 1H), 2.41–2.55 (m, 2H), 6.21 (s, 1H), 8.16 (s, 1H) ppm.

(ii) 4-Chloro-6-ethylpyrimidine

The product from Preparation 6(i) (348 g) was slurried in dichloromethane (2.5 L) and triethylamine (284 g) added. Phosphorus oxychloride (473 g) was added to the mixture and an exotherm resulted taking the reaction mixture to the reflux temperature. The reflux temperature was maintained for 4 hours and the reaction was then cooled to 20° C. and quenched into 1N aqueous hydrochloric acid solution (2.2 L) with applied cooling (maintaining the reaction temperature at about 10° C.). After separating the organic phase, the aqueous layer was extracted with dichloromethane (1 L). The organic phases were combined and washed with water (2×3 L). The solution was concentrated under reduced pressure to give the product (272 g, 80% purity by ¹H-NMR calculation) as a dark oil.

¹ H-NMR (300 MHz. CDCl₃): δ=1.31 (t, 3H), 2.80 (q, 2H), 7.23 (s, 1H), 8.88 (s, 1H) ppm.

(iii) 4-(1-Bromoethyl)-6-chloropyrimidine

The product from Preparation 6(ii) (212 g) was dissolved in dichloromethane (2.1 L). N-Bromosuccinimide (305.3 g) and azoisobutyronitrile (10.6 g) were added and the mixture was heated under reflux for 24 hours. Water (500 ml) was added and the heating under reflux was continued for a further 1 hour before cooling the mixture to 20° C. The organic phase was separated, washed with aqueous sodium metabisulphite solution (1 L) and then washed with water (1 L). The organic phase was dried with magnesium sulphate (20 g) and evaporated under reduced pressure to give the crude title compound as a dark oil (312 g, ca. 74% purity by ¹H-NMR calculation) that was used directly in Example 10.

¹H-NMR (300 MHz. CDCl₃): δ=2.03 (d, 3H), 5.04 (q, 1H), 7.51 (s, 1H). 8.95 (s, 1H) ppm.

PREPARATION 7

(2R,3S/2S,3R)-2-(2,4-Difluorophenyl)-3-(5-fluoro-pyrimidin-4-yl)-1-(1H-1,2,4-triazol-1-yl)butan-2-ol R-(−)-10-camphorsulphonate

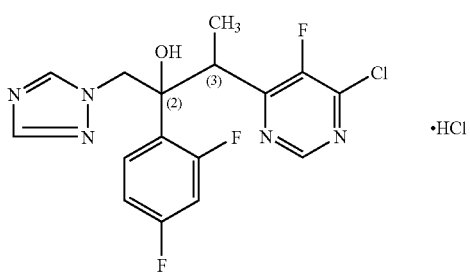

119:1 (2R, 3S/2S, 3R):(2R, 3R/2S, 3S)

(i) Pd/C, HCO₂NH₄, CH₃OH
(ii) R-(−)-10-camphorsulphonic acid

-continued

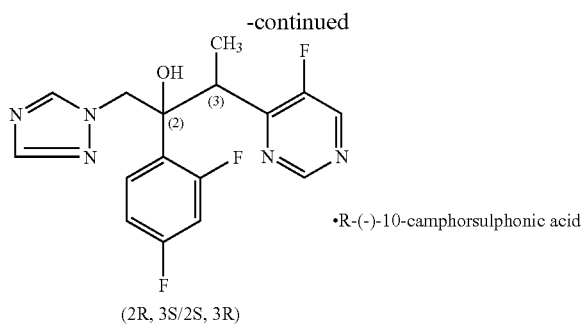

•R-(-)-10-camphorsulphonic acid (2R, 3S/2S, 3R)

119:1 (2R,3S/2S,3R)-:(2R,3R/2S,3S)-3-(4-Chloro-5-fluoropyrimidin-6-yl)-2-(2,4-difluorophenyl)-1-(1H-1,2,4-triazol-1-yl)butan-2-ol hydrochloride (40 g) was dissolved in methanol (360 ml). 10% w/w Palladium-on-carbon (50% w/w water content) (5.6 g) and ammonium formate (24 g) were added under an atmosphere of nitrogen. The reaction was heated under reflux for 2 hours and cooled to 25° C. The catalyst was removed by filtration and washed with methanol (120 ml). The filtrate was divided into two parts (2×ca. 245 ml).

One part was concentrated under reduced pressure and the residue dissolved in methylene chloride (95 ml) and water (95 ml) and stirred for 15 minutes. The organic layer was separated, washed with water (2×60 ml) and concentrated under reduced pressure to an oil. Isopropanol (100 ml) was added and the mixture concentrated under reduced pressure. Isopropanol (90 ml) was added and the mixture heated to 55° C. to give a solution. A solution of R-(-)-10-camphorsulphonic acid (10.75 g) in isopropanol (21.5 ml) was added to this solution. The resulting slurry was cooled to 25° C., granulated for 1 hour, cooled to 0° C. and granulated for a further 2 hours. The product was isolated by filtration, washed with cold isopropanol (2×20 ml) and dried under reduced pressure to provide the title compound (23.7 g). HPLC analysis using the conditions set out in Example 1 showed the product to be pure title compound.

PREPARATION 8

(2R,3S/2S,3R)-2-(2,4-Difluorophenyl)-3-(5-fluoropyrimidin-4-yl)-1-(1H-1,2,4-triazol-1-yl)butan-2-ol

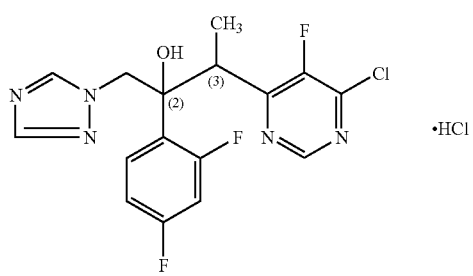

16.36:1 (2R, 3S/2S, 3R):(2R, 3R/2S, 3S)

(i) Basify
(ii) Pd/C, HCO$_2$NH$_4$, CH$_3$OH

-continued

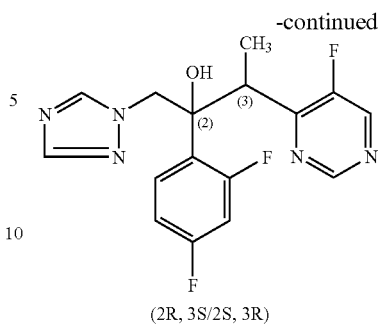

(2R, 3S/2S, 3R)

16.36:1 (2R,3S/2S,3R)-:(2R,3R/2S,3S)-3-(4-Chloro-5-fluoropyrimidin-6-yl)-2-(2,4-difluorophenyl)-1-(1H-1,2,4-triazol-1-yl)butan-2-ol hydrochloride (1.7 kg, containing solvent: proportion of (2R,3S/2S,3R) enantiomeric pair calculated to be 1.08 kg) was added to methylene chloride (8.5 L) and water (8.5 L) with stirring. The mixture was basified to pH 11 with 40% aqueous sodium hydroxide solution and the layers separated. The aqueous phase was extracted with methylene chloride (1.7 L). The combined organic extracts were washed with a solution of disodium ethylenediaminetetraacetic acid dihydrate (425 g) in water (8.5 L), and then water (2×5 L). The methylene chloride solution was divided into two unequal parts. Both parts were concentrated under reduced pressure to afford oils (containing 198 g and 980 g of the free bases, allowing for solvent, by $^1$H-NMR calculation). HPLC analysis using the conditions set out in Example 1 showed the oils to contain 76% and 69% by weight, respectively, of (2R,3S/2S,3R)-3-(4-chloro-5-fluoropyrimidin-6-yl)-2-(2,4-difluorophenyl)-1-(1H-1,2,4-triazol-1-yl)butan-2-ol.

The "980 g" sample was dissolved in methanol (10 L) and 10% w/w palladium-on-carbon (50% w/w water content) (Johnson Matthey type 87 L) (69 g) and ammonium formate (322 g) added under an atmosphere of nitrogen. The reaction was heated under reflux for 3 hours and cooled to 40° C. The catalyst was removed by filtration and the filtrate concentrated to an oil. Methylene chloride (5 L) and water (5 L) were added to the oil and the mixture stirred vigorously. The layers were separated and the aqueous layer was extracted with methylene chloride (1 L). The combined organic phases were washed with water (2×3 L), concentrated under reduced pressure, isopropanol added and again concentrated under reduced pressure. Isopropanol was added (3 L) and the slurry granulated at 0° C. for 1 hour. The product was collected by filtration, washed with isopropanol and dried under reduced pressure at 50° C. overnight to provide the title compound (547 g). HPLC analysis using the conditions set out in Example 1 showed the product to be 97% pure title compound.

PREPARATION 9

(2R,3S/2S,3R)-2-(2,4-Difluorophenyl)-3-(pyrimidin-4-yl)-1-(1H-1,2,4-triazol-1-yl)butan-2-ol

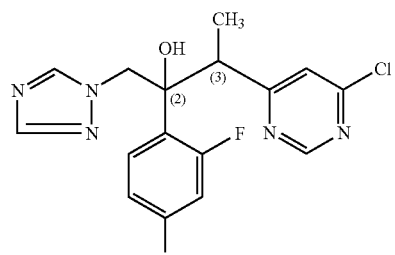

(2R, 3S/2S, 3R):(2R, 3R/2S, 3S)

| Pd/C, HCO$_2$NH$_4$, CH$_3$OH

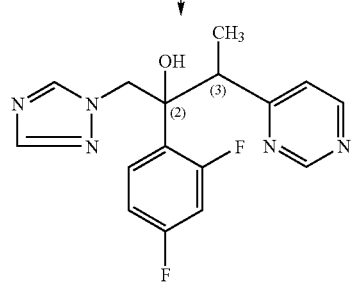

(2R, 3S/2S, 3R)

A mixture of (2R,3S/2S,3R)-:(2R,3R:2S,3S)-3-(4-chloropyrimidin-6-yl)-2-(2,4-difluorophenyl)-1-(1H-1,2,4-triazol-1-yl)butan-2-ol (the product of Example 10) (70 g), ammonium formate (24.1 g) and 10% w/w palladium-on-carbon (60% w/w water content) (Johnson Matthey type 87 L) (4.7 g) in methanol (700 ml) was heated under reflux for 2 hours under an atmosphere of nitrogen. After cooling to 25° C., the reaction was filtered and concentrated under reduced pressure. The residue was dissolved in dichloromethane (500 ml) and washed with water (2×500 ml). The organic phase was dried with magnesium sulphate, concentrated under reduced pressure and the resulting gum was crystallised from isopropanol (250 ml) at −10° C. The product was collected by filtration to give the title compound (38.1 g) after drying at 50° C. under reduced pressure.

$^1$H-NMR (300 MHz, CDCl$_3$): δ=1.1 (d, 3H), 3.65 (q, 1H), 4.15 (d, 1H), 4.8 (d, 1H), 6.55 (s, 1H), 6.8 (m, 2H), 7.4 (d, 1H), 7.5 (m, 1H), 7.6 (s, 1H), 7.9 (s, 1H), 8.75 (d, 1H), 9.15 (s, 1H) ppm.

The invention claimed is:

1. A process for the preparation of a compound of the formula:

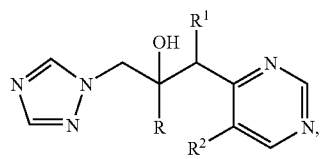

or an acid addition salt thereof, wherein

R is phenyl optionally substituted by 1 to 3 substituents each independently selected from halo and trifluoromethyl; $R^1$ is $C_1$–$C_6$ alkyl; and
$R^2$ is H or fluoro, which comprises the steps of:
(a) reaction of a compound of the formula:

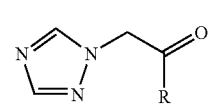

wherein R is as defined for a compound of the formula (IV), with a compound of the formula:

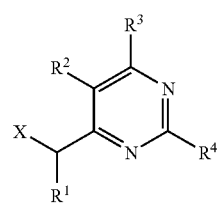

wherein X is chloro, bromo or iodo, $R^1$ and $R^2$ are as previously defined for a compound of the formula (IV) and either $R^3$ and $R^4$ are each independently selected from chloro and bromo or one of $R^3$ and $R^4$ is chloro or bromo and the other is H, in the presence of zinc,
iodine and/or a Lewis acid and an aprotic organic solvent, to provide a compound of the formula:

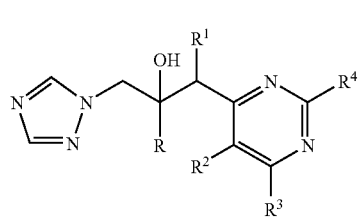

wherein R, $R^1$, $R^2$, $R^3$ and $R^4$ are as previously defined for this step (a);
(b) optionally converting the compound of the formula (IA) to an acid addition salt thereof;
(c) reduction of the compound of the formula (IA) or an acid addition salt thereof to provide the compound of the formula (IV); wherein the reduction in step (c) is carried out by catalytic hydrogenation or by transfer hydrogenation; and
(d) optionally reacting the compound of the formula (IV) with an acid to provide an acid addition salt thereof.

2. A process as claimed in claim 1 wherein lead is also present in step (a).

3. A process as claimed in claim 1 wherein in step (a) iodine is used.

4. A process as claimed in claim 1 wherein the aprotic organic solvent in step (a) is tetrahydrofuran.

5. A process as claimed in claim 1 wherein the acid addition salt in step (b) is the hydrochloride, methanesulphonate or p-toluenesulphonate salt.

6. A process as claimed in claim 1 wherein the reduction is carried out by transfer hydrogenation.

7. A process as claimed in claim 6 wherein the transfer hydrogenation is carried out using palladium and ammonium formate.

8. A process as claimed in claim 1 wherein the acid addition salt in step (d) is the S-(+)- or R-(−)-$^{10}$-camphorsulphonate salt.

9. A process as claimed in claim 1 wherein R is 2,4-difluorophenyl.

10. A process as claimed in claim 1 wherein $R^1$ is methyl.

11. A process as claimed in claim 1 wherein $R^2$ is fluoro.

12. A process as claimed in claim 1 wherein
(i) $R^3$ is chloro and $R^4$ is H;
(ii) $R^3$ is H and $R^4$ is chloro;
or (iii) $R^3$ and $R^4$ are both chloro.

13. A process as claimed in claim 12 wherein $R^3$ is chloro and $R^4$ is H.

14. A process as claimed in claim 1 wherein X is bromo.

15. A process as claimed in claim 1 wherein R is 2,4-difluorophenyl, $R^1$ is methyl, $R^2$ is fluoro, $R^3$ is chloro, $R^4$ is H and X is bromo.

16. A process as claimed in claim 1 wherein the compound of the formula (IA) is 3-(4-chloro-5-fluoropyrimidin-6-yl)-2-(2,4-difluorophenyl)-1-(1H-1,2,4-triazol-1-yl)butan-2-ol, 3-(2-chloro-5-fluoropyrimidin-6-yl)-2-(2,4-difluorophenyl)-1-(1H-1,2,4-triazol-1-yl)butan-2-ol, 3-(2,4-dichloro-5-fluoropyrimidin-6-yl)-2-(2,4-difluorophenyl)-1-(1H-1,2,4triazol-1-yl)butan-2-ol, or an acid addition salt of any thereof.

17. A process as claimed in claim 1 wherein the compound of the formula (IV) is 2-(2,4-difluorophenyl)-3-(5-fluoropyrimidin-4-yl)-1-(1H-1,2,4-triazol-1-yl)butan-2-ol or an acid addition salt thereof.

* * * * *